United States Patent
Braun et al.

(10) Patent No.: US 7,319,175 B2
(45) Date of Patent: Jan. 15, 2008

(54) CATALYST SYNTHESIS OF HALOGENATED COMPOUNDS WITH CATALYST REGENERATION WITH ELEMENTAL HALOGEN

(75) Inventors: Max Braun, Wedemark (DE); Carsten Brosch, Seelze (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 11/259,138

(22) Filed: Oct. 27, 2005

(65) Prior Publication Data

US 2006/0036118 A1 Feb. 16, 2006

Related U.S. Application Data

(63) Continuation of application No. 10/870,425, filed on Jun. 18, 2004, now Pat. No. 7,074,975, which is a continuation of application No. PCT/EP02/14220, filed on Dec. 13, 2002.

(30) Foreign Application Priority Data

Dec. 21, 2001 (DE) ................................ 101 63 170

(51) Int. Cl.
*C07C 17/08* (2006.01)
(52) U.S. Cl. ...................................... 570/167; 570/170
(58) Field of Classification Search ................ 570/134, 570/136, 161, 164, 165, 167, 170, 175; 502/22, 502/29, 32
See application file for complete search history.

(56) References Cited

U.S. PATENT DOCUMENTS

| 2,005,710 A | | 6/1935 | Alexander et al. |
| 2,510,872 A | | 6/1950 | Downing |
| 2,759,026 A | | 8/1956 | McCleary |
| 4,147,733 A | | 4/1979 | Fiske et al. |
| 5,105,033 A | * | 4/1992 | Swearingen et al. ........ 570/166 |
| 5,714,650 A | * | 2/1998 | Wuttke ...................... 570/165 |
| 6,034,016 A | * | 3/2000 | Boyce et al. ................. 502/20 |

FOREIGN PATENT DOCUMENTS

GB 589167 6/1947

* cited by examiner

*Primary Examiner*—Karl Puttlitz
(74) *Attorney, Agent, or Firm*—Crowell & Moring LLP

(57) ABSTRACT

Catalysts such as antimony halides, which are useful in fluorination reactions involving hydrogen fluoride, may be reduced during the reaction and require regeneration. Regenerative oxidation is usually carried out by introducing elemental halogen, preferably fluorine or chlorine, into the reaction mixture. In accordance with the invention elemental halogen is prevented from coming into contact with starting materials or intermediate products which are reactive therewith. This is preferably achieved by withdrawing part of the reaction mixture from the reactor, mixing the withdrawn part with chlorine or fluorine in order to regenerate the catalyst, and thereafter returning the withdrawn part to the reactor.

16 Claims, No Drawings

CATALYST SYNTHESIS OF HALOGENATED COMPOUNDS WITH CATALYST REGENERATION WITH ELEMENTAL HALOGEN

CROSS REFERENCE TO RELATED APPLICATIONS

This application is a continuation of U.S. patent application Ser. No. 10/870,425, filed Jun. 18, 2004 now U.S. Pat. No. 7,074,975, which is a continuation of international patent application no. PCT/EP02/14220, filed Dec. 13, 2002, designating the United States of America and published in German as WO 03/053580, the entire disclosures of which are incorporated herein by reference. Priority is claimed based on Federal Republic of Germany patent application no. DE 101 63 170.7, filed Dec. 21, 2001.

BACKGROUND OF THE INVENTION

The present invention relates to a method for the catalyzed synthesis of partially halogenated, fluorine-containing organic compounds with regeneration of the catalyst used.

It has long been known that fluorine-containing organic compounds can be synthesized by a halogen-fluorine exchange or by the addition of hydrogen fluoride using hydrogen fluoride in the presence of a catalyst. U.S. Pat. No. 2,005,710 discloses the synthesis of many alkanes containing fluorine, chlorine and optionally hydrogen. Antimony halide catalysts are described as preferred. If a pentavalent catalyst is reduced to the trivalent form, it is desirable that free halogen, such as chlorine, be present during the reaction or added at an arbitrary time (see column 13, lines 32 to 37 of U.S. Pat. No. 2,005,710). This method of regenerating the catalyst in fluorination processes using hydrogen fluoride is described in U.S. Pat. No. 2,510,872 as the state of the art which is to be improved. In the method described in U.S. Pat. No. 2,510,872, antimony pentafluoride is used. However, it is used there not as a catalyst, but as a fluorinating agent.

It has now proved possible to establish that the presence of elemental halogen, such as chlorine, is disadvantageous for the purpose of regenerating the reduced catalyst in the reactor when organic compounds are present which react with the halogen in an undesirable manner, for example, with elemental chlorine with the addition of the chlorine.

SUMMARY OF THE INVENTION

It is an object of the present invention to provide an improved method for the synthesis of partially halogenated fluorine-containing organic compounds with regeneration of the catalyst by oxidation with elemental halogen, preferably with chlorine.

This and other objects are achieved in accordance with the present invention by providing a method for synthesizing partially halogenated, fluorine-containing organic compounds by halogen-fluorine exchange or addition of hydrogen fluoride using hydrogen fluoride in the presence of a catalyst, wherein used catalyst is regenerated by reacting the catalyst with elemental halogen, and wherein the regeneration is carried out such the elemental halogen does not come into contact with organic starting materials or intermediate products which react with elemental halogen to form undesired by-products.

In the method according to the invention for synthesizing partially halogenated, fluorine-containing organic compounds by halogen-fluorine exchange or by the addition of hydrogen fluoride using hydrogen fluoride in the presence of catalysts, which are regenerated with elemental halogen, the regeneration is carried out so that the elemental halogen does not come into contact with starting materials or intermediates, which can react with halogen in an undesirable manner.

It will be apparent to persons skilled in the art that it is frequently not possible to completely prevent contact between the halogen and the undesirably reactive starting materials or intermediates. It is sufficient to carry out the regeneration so that the halogen does not come into contact with substantial amounts of undesirably reactive starting materials or intermediates. As used herein, the term "substantial" refers to those amounts, which cause more than 10% by weight, preferably more than 5% by weight and, particularly preferably, more than 2% by weight of the starting material to be reacted finally to undesirable by-products.

The term "undesirably reactive" refers to those compounds, which react more quickly with the elemental halogen than does the antimony(III) compound which is to be regenerated, or which form by-products in undesirable amounts. For example, a compound can be regarded as "undesirably reactive" if more than 10% by weight, preferably more than 5% by weight, and particularly preferably more than 2% by weight, of the starting material leads to undesirable by-products.

Preferably, the regeneration is carried out so that not more than 10% by weight, preferably not more than 5% by weight, and particularly preferably not more than 2% by weight, of the starting material is converted into undesirable by-product.

There are various possibilities for carrying out the method of the invention in order to achieve the desired effect of the invention. For example, it is possible to work batchwise and to permit at least the undesirably reactive organic compounds to react, or to remove these compounds from the reactor, for example, by distillation or decanting, before commencing the introduction of halogen for the regeneration. Of course, unreactive compounds, such as unreactive products, may also be removed at the same time. If then at most insignificant amounts of reactive compounds remain in the reactor, the regeneration can be commenced by introducing halogen.

Preferably, a portion of the reaction mixture is removed from the reactor through a loop.

In the preferred method of synthesizing partially halogenated, fluorine-containing organic compounds by halogen-fluorine exchange or by the addition of hydrogen fluoride using hydrogen fluoride in the presence of catalysts which are regenerated with elemental halogen, a portion of the reaction mixture is removed from the reactor, and the removed portion is reacted with halogen in order to regenerate the catalyst. The removed portion, having been so treated, is returned to the reactor together with the regenerated catalyst. The preferred halogens include chlorine and fluorine, particularly chlorine.

The method can be carried out in such a way that a portion of the reaction mixture is removed continuously, semi-continuously or at particular times.

Preferably, the synthesis method is one in which a bromine-fluorine exchange or, in particular, a chlorine-fluorine exchange is carried out. Optionally, there may also be a further addition of hydrogen fluoride.

The preferred catalyst is antimony pentachloride or a fluorination product or hydrogen fluoride adduct thereof.

The fluorination products correspond to the general formula $SbF_xCl_{5-x}$, in which x is 0 to 5.

The method is particularly advantageous if the partially halogenated, fluorine-containing organic compounds synthesized, the starting materials and/or any intermediates react with elemental chlorine in an undesirable manner. This is especially the case if starting materials are used, which have unsaturated bonds, since such bonds react readily with chlorine. Examples include C=C double bonds.

However, the method is also advantageous if saturated starting materials are used. Halogen exchange reactions frequently take place by an elimination-addition mechanism, or such a mechanism takes place in addition to an SN mechanism. The unsaturated intermediates, formed by an elimination, also react more easily with chlorine to form undesirable products. However, the foregoing explanation is not intended to limit the scope of the invention.

The method is particularly preferred for the synthesis of aliphatic, fluorohydrocarbons or aliphatic chlorofluorohydrocarbons, especially those with 1 to 10 carbon atoms. The synthesis of aliphatic C1-C5 fluoro(chloro)hydrocarbons, particularly aliphatic C1-C4 fluoro(chloro)hydrocarbons is especially preferred.

Examples of compounds which can be synthesized and of the starting materials from which they are produced include:

| Product | | Starting Material |
|---|---|---|
| $CF_3CH_2CHF_2$ | from | $CCl_3$—CH=CHCl + 5 HF |
| $CF_3CH_2CH_2$—$CH_3$ | from | $CCl_3$—$CH_2$—$CCl_2$—$CH3$ + 5 HF |
| $CF_3CH_2CF_2CH_3$ | from | $CCl_3$—$CH_2$—CCl=$CH3$ + 5 HF |
| $CH_2F_2$ | from | $CH_2Cl_2$ + 2 HF |
| $CFCl_2$—$CH_2Cl$ | from | $CCl_2$=CHCl + HF |
| $CCl_2F$—$CHCl_2$ | from | $CCl_2$=$CCl_2$ + HF |
| $CClF_2$—$CHCl_2$ | from | $CCl_2$=$CCl_2$ + 2 HF |
| $CF_3$—$CHCl_2$ | from | $CCl_2$=$CCl_2$ + 3 HF |
| $CF_3$—$CHF_2$ | from | $CCl_2$=$CCl_2$ + 5 HF |
| $CF_3CH_2F$ | from | $CCl_2$=CHCl + 4 HF |
| $CFCl_2$—$CH_3$ | from | $CCl_2$=$CH_2$ + HF |
| $CHF_2$—$CH_3$ | from | CHF=$CH_2$ |
| $CF_2Cl$—$CH_3$ | from | $CCl_2$=$CH_2$ |
| $CF_3$—$CH_3$ | from | $CF_2$=$CH_2$ |
| $CHClF_2$ | from | $CHCl_3$ + 2 HF, and |
| $CHF_3$ | from | $CHCl_3$ + 3 HF. |

Preferably, the inventive method is carried out so that a liquid phase is present in the reactor. The pressure and temperature are adjusted appropriately. The pressure in the reactor preferably ranges from 1 to 15 bar, and particularly preferably from 10 to 15 bar. The temperature preferably ranges from 10° to 200° C.; particularly preferably from 70° to 150° C., and especially preferably from 90° to 120° C.

The molar ratio of hydrogen fluoride to catalyst desirably ranges from 1:1 to 30:1, and preferably lies in the range from 8:1 to 5:1. The molar ratio of catalyst to organic starting material desirably ranges from 0.1:1 to 20:1, and preferably will lie in the range from 1:1 to 3:1.

The continuous removal is carried out so that, at all times, 5 to 20 mole percent of the catalyst are removed, the same percentage also being removed in the semi-continuous or batchwise procedure.

It is an advantage of the method according to the invention that the chlorine (or halogen) is not introduced directly into the fluorination reactor, where it could lead to side reactions with starting materials, intermediates or end products.

In principle, the method can be used for any fluorination reactions. It can also be used for fluorination reactions, in which aromatic compounds (which are regarded here as "partially halogenated") participate. The use of the method for the synthesis of saturated or unsaturated aliphatic fluorohydrocarbons or of chlorofluorohydrocarbons with 1 to 10 and preferably 1 to 5 carbon atoms is particularly preferred. The advantages of the method according to the invention are especially apparent if starting materials are used, which react very readily with elemental halogen, especially with chlorine, as is the case, for example, with unsaturated starting materials (halogenated ethenes, propenes, butenes, etc.). In addition, care must be taken that the content of starting materials or intermediates which react with chlorine, is very small or that such compounds are not present at all in the removed portion during the addition of chlorine. For this purpose, there are at least two possible measures.

One possible measure is to remove a portion of the contents of the reactor once the starting material or intermediate, which reacts readily with chlorine, has been reacted to form less sensitive compounds. Such a method is a semi-continuous method in which the starting material, which reacts undesirably with chlorine, is added once the regeneration of the catalyst is ended and in which the regeneration of the catalyst is carried out when the starting material in question has finished reacting.

A second possible measure involves reducing the pressure on the removed portion, for example, to less than 5 bar, or even to less than 2 bar or to a lower value. Volatile organic and inorganic compounds, including the starting material which reacts undesirably with chlorine, are removed in gaseous or vapor form from the portion which has been removed from the reactor. Only then is the regeneration of the catalyst commenced.

This can also be carried out so that the product is isolated, for example, in a distillation apparatus. The fluorinated product usually is more volatile than the starting material. It can be separated from hydrogen chloride or hydrogen fluoride by conventional methods. Any starting materials present, especially if these are unsaturated compounds, are then also removed. The remaining material, which contains the catalyst, is then treated with chlorine (or halogen) in order to regenerate the catalyst in this way.

A further aspect of the invention relates to the control of the fluorination reaction so that products are produced which are fluorinated to a greater or lesser extent. It has been found that the proportion of Sb(III), in relation to the total Sb(V)/Sb(III), has an effect on the catalytic properties of the antimony catalyst. The higher the proportion of Sb(V), the greater the effect with regard to the formation of more highly fluorinated products will be. In the method according to the invention, the proportion of Sb(III) can be affected, for example, due to the fact that the partial amount removed is decreased or by increasing the amount of chorine added relative to the partial amount of reaction mixture which is removed, so that there is a pre-determined proportion of Sb(III) in the reactor. In this way, the formation of less highly fluorinated products is promoted. In order to promote the formation of more highly fluorinated products, the partial amount removed or the addition of chlorine is increased.

The following examples are intended to illustrate the invention in further detail without limiting the scope of the invention.

EXAMPLE 1

Synthesis of Dichlorotrifluoroethane (HCFC-123)

Pentachloroethane, antimony pentafluoride and hydrogen fluoride were introduced into a continuous, mobile autoclave. The molar ratio of HF to $SbF_5$ was about 12:1, and the molar ratio of $SbF_5$ was 5:1. The autoclave was then brought to a temperature of 100° C. and a pressure of 15 bar. A portion of the contents of the reactor (approximately 15 mole percent of the catalyst) was withdrawn continuously from the reactor (autoclave) and transferred to a stripper column. Organic components (especially HCFC-121, HCFC-122 and HCFC-123, as well as pentachloroethane) were removed together with hydrogen fluoride and hydrogen chloride by reducing the pressure, and the removed components were returned to the autoclave. The remaining portion from the stripper column was treated countercurrently with elemental chlorine in order to regenerate the catalyst.

It is an advantage of the low reaction temperature (90° to 120° C.) that the tendency of Sb(V) to form Sb(III) is greatly reduced.

EXAMPLE 2

Synthesis of Dichlorotrifluoroethane with Chlorination after the Perchloroethylene has been Reacted Perchloroethylene (0.05 moles) was transferred to an autoclave with a polytetrafluoroethylene liner and treated slowly with antimony pentafluoride (0.1 moles) and hydrogen fluoride (0.88 moles). The autoclave was closed and placed for 1 hour, with stirring, in an oil bath heated to 120° C. During this time, the perchloroethylene reacted completely.

After the autoclave had been cooled to room temperature, the pressure of the gas phase was relieved, and 5.4 g of chlorine gas (0.08 moles, 80 mole percent based on the antimony) was introduced into the autoclave (pressure: 4.9 bar). After 5 minutes with stirring, the pressure had dropped to 3.9 bar. The pressure remained stable for a further 3 hours. The autoclave was then cooled in ice; the pressure of the gas phase was relieved, and the autoclave was opened. The formulation was hydrolyzed in a mixture of ice and tartaric acid. The organic material was separated from the aqueous phase, and both where analyzed.

| Analysis of Organic Material | Isomers | Catalyst Analysis |
|---|---|---|
| 00.01 area-% 124a | 99.87 area-% 123 | 55.93 mole-% $SbF_5$ |
| 57.15 area-% 123 | 00.13 area-% 123a | 34.27 mole-% HF |
| 00.72 area-% 113 | | 09.80 mole-% HCl |
| 41.97 area-% 122 | | No $SbF_3$ detectable |
| 00.15 area-% other | | |
| Conversion of perchloroethylene = 100% | | |
| Selectivity for 123, 122, 121 = 99.13% | | |

This example confirms the advantageousness of the procedure of chlorinating only after the pentachloroethylene has reacted. It also shows that the saturated end products are not "undesirably reactive".

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A liquid-phase method for synthesizing partially halogenated, fluorine-containing organic compounds from saturated starting material or starting material having unsaturated bonds by halogen-fluorine exchange or addition of hydrogen fluoride using hydrogen fluoride in the presence of an Sb(V) catalyst, wherein used catalyst which is reduced to Sb(III) is regenerated by oxidation by reacting the catalyst with elemental halogen, comprising the step of providing a reaction mixture comprising used catalyst, partially halogenated, fluorine-containing organic compounds synthesized from the starting material and optionally starting material or unsaturated intermediates, wherein the regeneration is carried out such that elemental halogen does not come into contact with organic starting materials or intermediate products so that at most 10% by weight of the starting material is converted to undesired side products, and wherein the regeneration is carried out by introducing the elemental halogen into said reaction mixture after starting material or unsaturated intermediates are permitted to react.

2. A method according to claim 1, wherein the catalyst is regenerated by reacting the catalyst with elemental chlorine.

3. A method according to claim 1, wherein the synthesis is effected by exchanging fluorine for bromine or chlorine.

4. A method according to claim 3, wherein a halogen-fluorine exchange and addition of HF to unsaturated bonds of the starting material is performed.

5. A method according to claim 1, wherein the catalyst comprises antimony pentachloride, a fluorination product of antimony pentafluoride, or a hydrogen fluoride adduct of antimony pentafluoride.

6. A method according to claim 1, wherein said partially halogenated, fluorine-containing organic compound is an aliphatic, fluorohydro-carbon or aliphatic chlorofluorohydrocarbon of 1 to 10 carbon atoms.

7. A method according to claim 6, wherein the partially halogenated, fluorine-containing organic compound is an aliphatic C1-C5 fluoro(chloro)hydrocarbon.

8. A method according to claim 6, wherein the partially halogenated fluorine-containing organic compound is an aliphatic C1-C4 fluoro (chloro)hydrocarbon.

9. A method according to claim 1, wherein fluoroethanes or chlorofluoroethanes are synthesized from chloroethenes or from chlorofluoroethenes.

10. A method according to claim 1, wherein the synthesis reaction pressure lies in the range from 1 to 15 bar, and the synthesis reaction temperature lies in the range from 20° to 200° C.

11. A method according to claim 10, wherein the synthesis reaction pressure lies in the range from 10 to 15 bar, and the synthesis reaction temperature lies in the range from 70° to 150° C.

12. A method according to claim 11, wherein hydrogen fluoride and catalyst are present in a molar ratio of from 1:1 to 30:1.

13. A method according to claim 12, wherein the molar ratio of hydrogen fluoride to catalyst lies in the range from 8:1 to 15:1.

14. A method according to claim 1, wherein catalyst and organic starting material are present in a molar ratio of from 0.1:1 to 20:1.

15. A method according to claim 14, wherein the molar ratio of catalyst to organic starting material lies in the range from 1:1 to 3:1.

16. A method according to claim 1, wherein the degree of regeneration of the catalyst is controlled in order to regulate the degree of fluorination of the partially halogenated, fluorine-containing organic compound which is synthesized in the presence of the regenerated catalyst, the degree of regeneration of the catalyst having been controlled.

* * * * *